United States Patent [19]

Ohsaki et al.

[11] Patent Number: 5,903,352
[45] Date of Patent: May 11, 1999

[54] APPARATUS AND METHOD FOR MEASURING OPTICAL ANISOTROPY

[75] Inventors: Yoshinori Ohsaki, Machida; Takashi Suzuki, Yokohama, both of Japan

[73] Assignee: Canon Kabushiki Kaisha, Tokyo, Japan

[21] Appl. No.: 08/592,861

[22] Filed: Jan. 24, 1996

[30] Foreign Application Priority Data

| Jan. 27, 1995 | [JP] | Japan | 7-012105 |
| Aug. 9, 1995 | [JP] | Japan | 7-203386 |
| Aug. 24, 1995 | [JP] | Japan | 7-216354 |

[51] Int. Cl.$^6$ ............................... G01J 4/00; G02F 1/01
[52] U.S. Cl. .......................... 356/364; 250/225
[58] Field of Search .................. 356/364, 365, 356/366, 367; 359/93, 94; 250/225

[56] References Cited

U.S. PATENT DOCUMENTS

| 4,786,802 | 11/1988 | Yoshii et al. | 250/225 |
| 4,799,796 | 1/1989 | Musha | 356/336 |
| 5,071,229 | 12/1991 | Oaki et al. | 359/53 |
| 5,394,245 | 2/1995 | Sato | 356/369 |
| 5,434,671 | 7/1995 | Sumiyoshi et al. | 356/367 |

FOREIGN PATENT DOCUMENTS

| 42 11 467 | 10/1993 | Germany . |
| 1-169340 | 7/1989 | Japan . |
| 6-074864 | 3/1994 | Japan . |

OTHER PUBLICATIONS

F. Nakano, et al., "Simple Method of Determining Liquid Crystal Tilt–Bias Angle", Jpn. J. Appl. Phys., vol. 19, No. 10, pp. 2013–2014 (1980)( No Month Available).

K.Y. Han, et al., "Accurate Determination and Measurement Error of Pretilt Angle in Liquid Crystal Cell", Jpn. J. Appl. Phys., vol. 32, pp. L277–L279 (1993) (No Month Available).

Scheffer T.J., et al., "Accurate Determination of Liquid–Crystal Tilt Bias angles", Journal of Applied Physics, vol. 48, No. 5, pp. 1783–1792 (May 1977).

Francon M., "Handbuch der Physik", vol. XXIV, pp. 432–447, figs. 407, 408 (1956).

Yamashita, M., "Dependence of Temporal Behavior of Conoscopic Figures in Nematic Liquid Crystals on Film Thickness", Japanese Journal of Applied Physics, Part 1, vol. 25, No. 1, pp. 1–7 (Jan. 1986).

Han K–Y, et al., "Determination of Molecular Inclination in Rubbed Polymer for Liquid Crystal Alignment by Measuring Retardation", Japanese Journal of Applied Physics, Part 2, vol. 32, No. 9A, pp. L1242–L1244 (Sep. 1993).

Hughes, J.R., "Automatic Electrooptic Bench for the Characterization of Liquid Crystal Mateials and Devices", Displays, Technology and Applications, vol. 6, No. 4, pp. 212–217 (Oct. 1985).

*Primary Examiner*—Frank G. Font
*Assistant Examiner*—Zandver V. Smith
*Attorney, Agent, or Firm*—Fitzpatrick, Cella, Harper & Scinto

[57] ABSTRACT

An optical anisotropy measurement apparatus including a light source emitting a light beam and a photodetector disposed opposite to the light source is provided for measuring an optical anisotropy of an object to be examined disposed between the light source and the photodetector so as to intersect a straight line connecting the light source and the photodetector. The apparatus further includes: a supporting member for supporting the object to be examined rotatably about a rotation axis extending perpendicular to the straight line, a polarizer positioned between the light source and the object to be examined, an analyzer positioned between the object to be examined and the photodetector, and an optical member disposed between the light source and the object to be examined so as to cause the beam to pass through an intersection of the straight line and the rotation axis. The optical member is preferably a pair of transparent members each having a curved surface and a flat surface disposed to sandwich the object to be examined with their opposing flat surfaces. The object to be examined may be a liquid crystal cell.

40 Claims, 8 Drawing Sheets

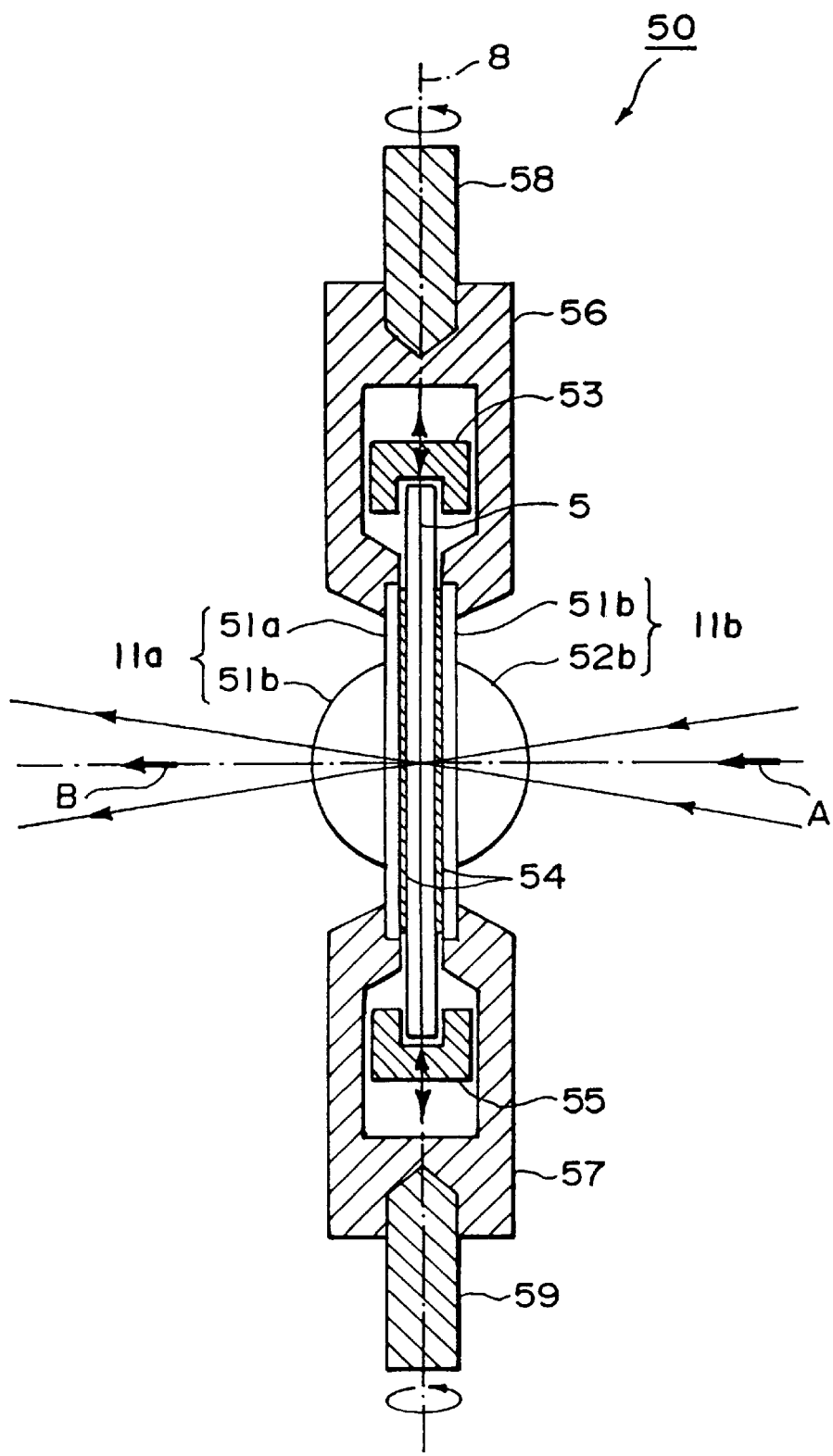
F I G. 5

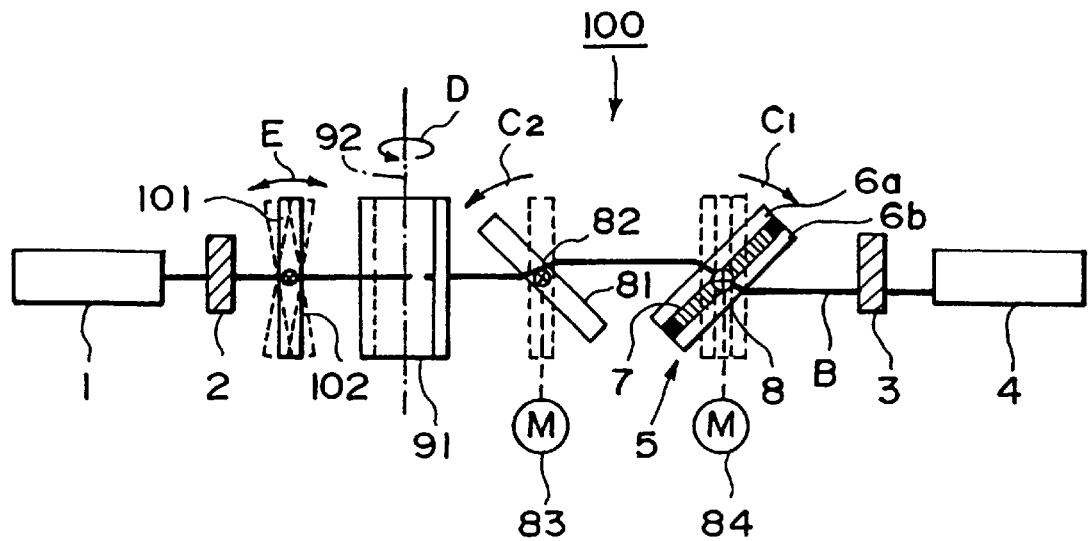
F I G. 10
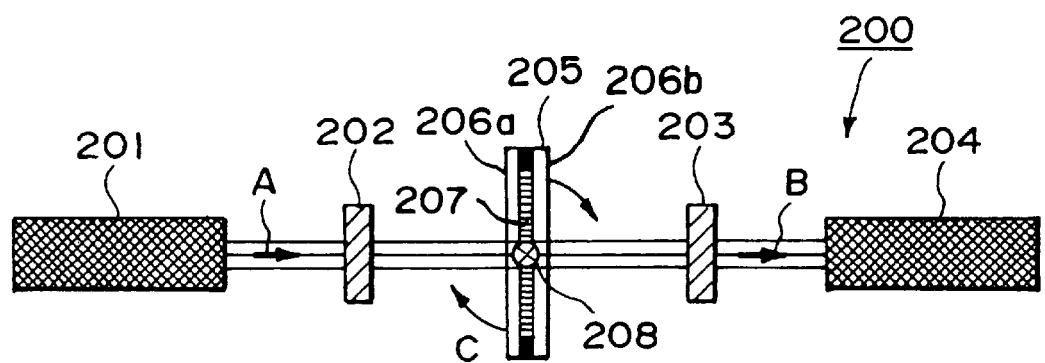
F I G. 11

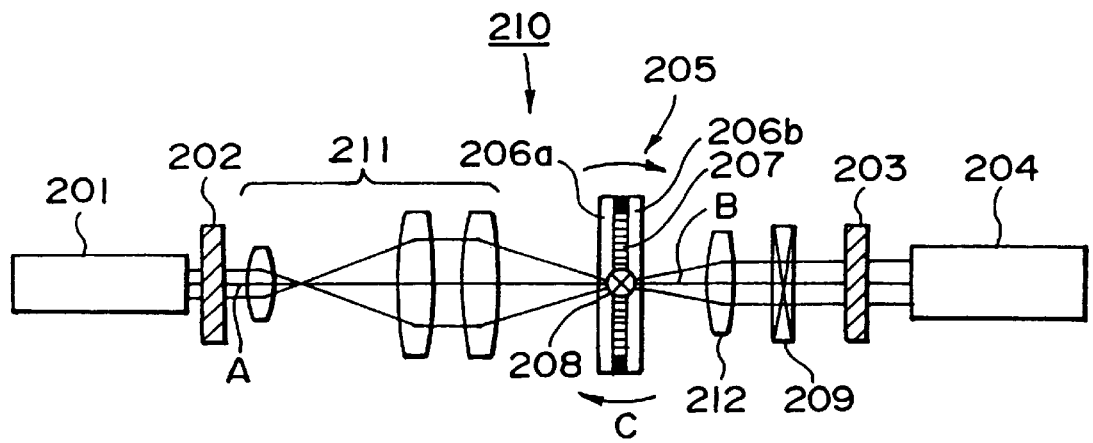
F I G. 14
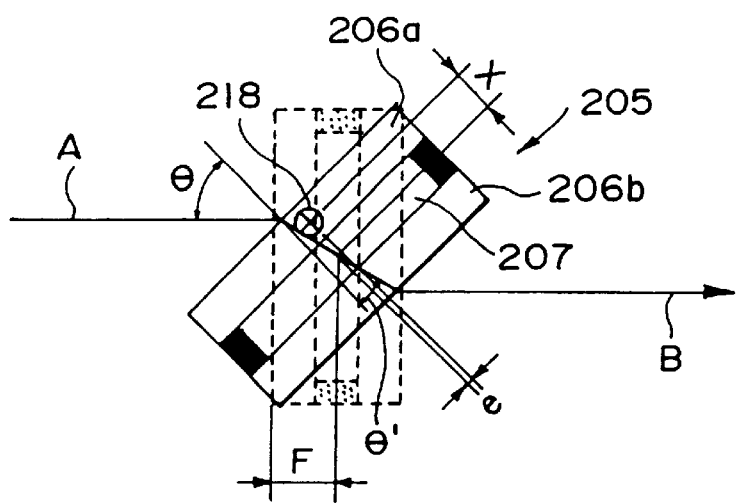
F I G. 15

APPARATUS AND METHOD FOR MEASURING OPTICAL ANISOTROPY

FIELD OF THE INVENTION AND RELATED ART

The present invention relates to an apparatus and a method for measuring the optical anisotropy of a substance. More particularly, the present invention relates to an apparatus and a method for measuring an optical anisotropy of a liquid crystal in order to determine a pretilt angle of the liquid crystal, and a process for producing a liquid crystal device by using the optical anisotropy measurement apparatus.

In production of a liquid crystal device, a treatment for aligning liquid crystal molecules such as rubbing has been generally performed. By the aligning treatment, liquid crystal molecules are aligned to form a certain angle (called a pretilt angle), with respect to a substrate surface in a liquid crystal device. The magnitude of the pretilt angle and a fluctuation thereof in a liquid crystal device are one of major factors determining the optical performance of the liquid crystal device. Further, in contrast with a solid-state crystal, a liquid crystal is liable to result in more or less locally different pretilt angles. It is generally preferred, however, that the pretilt angle is uniform in a liquid crystal device. Accordingly, the measurement of a pretilt angle of a liquid crystal and a deviation or distribution thereof in a liquid crystal device is important in development and production control of liquid crystal devices.

For the above reason, it has been known to measure an optical anisotropy of a liquid crystal to calculate a pretilt angle, e.g., by using a crystal rotation method (Jpn. J. Appl. Phys., Vol. 19 (1980), No. 10, Shote Notes 2013).

FIG. 11 shows an example of known optical anisotropy measurement apparatus according to the crystal rotation method. Referring to FIG. 11, an optical anisotropy measurement apparatus 200 includes a He-Ne laser 201, a polarizer 202, an analyzer 203 and a photodetector 204, and a liquid crystal cell 205 as an object to be examined is disposed between the polarizer 202 and the analyzer 203. The liquid crystal cell 205 comprises a pair of glass substrates 206a and 206b respectively having thereon alignment films (of, e.g., ca. 0.02 μm-thick polyimide films having a refractive index of ca. 1.6, not shown), and a liquid crystal layer 207 of, e.g., 1–20 μm in thickness sealed between the alignment films. The liquid crystal cell 205 is supported rotatably about a rotation axis 208 extending in a direction perpendicular to a central axis of an incident beam A (laser beam, parallel light flux) emitted from the He-Ne laser 201 (i.e., in a direction perpendicular to the drawing). In case where the alignment films are subjected to a uniaxial aligning treatment, the uniaxial alignment axis is disposed perpendicular to the rotation axis 208.

Now, the principle of optical anisotropy measurement (principle of pretilt angle determination) for a liquid crystal layer 207 by using the conventional optical anisotropy measurement apparatus 200 according to the crystal rotation method will be described.

An incident beam A emitted from the He-Ne laser 201 passes through the polarizer 202 to be transformed into linear polarized light and enters the liquid crystal cell 205. The incident beam A having entered the liquid crystal cell 205 interacts with liquid crystal molecules therein to change its polarization state, i.e., to generally form elliptically polarized light and go out of the liquid crystal cell 205. The outgoing beam emitted from the liquid crystal cell 205 passes though the analyzer 203 having ia polarization direction parallel or perpendicular to that of the analyzer 203 to reach the photodetector 204.

When the liquid crystal cell 205 supported rotatably about the rotation axis 208 extending perpendicular to the central axis of the incident beam A (and vertical to the drawing) is rotated, e.g., in a clockwise direction, the director of liquid crystal molecules (which is a unit vector representing the orientation direction of liquid crystal molecules) is changed relative to the electric field direction of the incident beam A. Accordingly, corresponding to the rotation angle of the liquid crystal cell 205, the polarization state of the outgoing beam B going out of the liquid crystal cell 205 is changed.

By plotting the outputs of the photodetector 204 versus the rotation angle of the liquid crystal cell 205, a characteristic curve as shown in FIG. 12 can be obtained. In this instance, as the manner or behavior of polarization state change versus the rotation axis 208 varies depending on the magnitude of the pretilt angle, it is possible to determine a pretilt angle from the characteristic curve.

More specifically, a pretilt angle may be determined based on a characteristic curve as shown in FIG. 12 obtained, e.g., by using a liquid crystal cell obtained by rubbing the alignment films formed on the glass substrates 206a and 206b of the liquid crystal cell 205 in directions which are parallel but opposite to each other, and disposing the polarizer 202 and the analyzer 203 so that their mutually crossing polarization directions form angles of 45 deg. with respect to the rotation axis 208. The characteristic curve is compared with the following two theoretical equations:

$$T(\theta) = \cos^2[(\pi d/\lambda)((n_o n_e(n^2(\alpha) - \sin^2\theta)^{1/2} / \qquad (1)$$
$$n^2(\alpha) - (n_o^2 - \sin^2\theta)^{1/2}) - [(n_e^2 - n_o^2)/$$
$$n^2(\alpha)] \cdot \sin\alpha \cdot \cos\alpha \cdot \sin\theta)]$$
$$n(\alpha) = (n_o^2\cos^2\alpha + n_e^2\sin^2\alpha)^{1/2}, \qquad (2)$$

wherein $n_o$ and $n_e$: refractive indices for ordinary rays and extraordinary rays, respectively, of the liquid crystal, $\theta$: rotation angle of the liquid crystal cell 205, $\alpha$: pretilt angle, $t(\theta)$: transmitted light intensity, d: thickness of the liquid crystal layer 207 and $\lambda$: wavelength of the incident beam A.

In the above equations, $n_o$, $n_e$ and $\lambda$ are known values, and the pattern of the curve shown in FIG. 12 depends on $\alpha$ and d.

Accordingly, the theoretically calculated curves of $T(\theta)$ are obtained by successively changing $\alpha$ and d in the equations (1) and (2) to determine optimum values of $\alpha$ and d so that the peaks and the valleys of the calculated curve best fit those of the pattern shown in FIG. 12 based on the measured data, e.g., by using the least square method.

Incidentally, in the above-described measurement, the rotation angle of the liquid crystal cell ranges over ±60–70 degrees (giving a width of 120–140 degrees) if the angle is taken at 0 degrees when the incident beam A enters perpendicularly (the state shown in FIG. 11).

As described above, the optical anisotropy measurement apparatus 200 allows the measurement of an optical anisotropy of a liquid crystal layer 207 based on the measurement of a change in polarization state of the beam B going out of the liquid crystal cell 205 caused by interaction of the incident beam A with the liquid crystal molecules in the liquid crystal layer 207, and the determination of a pretilt angle based on the measured optical anisotropy.

The optical anisotropy measurement apparatus 200 may be used not only for determination of a pretilt angle of a liquid crystal but also for measuring optical anisotropy of other substances.

Incidentally, in the optical anisotropy measurement by using the above-mentioned optical anisotropy measurement apparatus 200, the region for optical anisotropy measurement is also deviated by the rotation of the liquid crystal cell 205. More specifically, if the incident beam A enters the liquid crystal cell 205 perpendicularly to the substrate thereof as shown in FIG. 11, the incident beam A does not cause refraction. However, if the liquid crystal cell 205 is rotated for measurement of optical anisotropy of the liquid crystal layer 207 as shown in FIG. 13, the incident angle of the beam incident to the glass substrate 206a on the incidence side is changed, whereby the beam A is refracted at the surface of the substrate 206a. The degree of refraction changes depending on the rotation angle of the liquid crystal cell 205, so that the pretilt angle measurement region is changed corresponding to the rotation angle. As a result, a deviation e in measurement position occurs.

More specifically, in case where the incidence side glass substrate 206a has a thickness of 1 mm and a refractive index of 1.5, the deviation in measurement position amounts to ca. 2 mm when the liquid crystal cell is rotated at an angle of 70 deg. In an actual measurement, the cell is rotated also in the other direction, the deviation in measurement position totally amounts to 4 mm. In view of the fact that the inside beam A emitted from the He-Ne has a beam diameter of ca. 1 mm, the deviation of 4 mm is substantially large, so that it is understood that the optical anisotropy measurement region is drastically changed corresponding to the rotation of the liquid crystal cell 205.

Further, an ordinary liquid crystal device used for display, etc., may comprise several hundreds of thousand to several million minute pixels, each having a square size on the order of several tens to several hundreds $\mu$m square. In a liquid crystal device different from a crystal, a total irregularity, such as locally different pretilt angles, is liable to occur. For example, in production of an active matrix-type liquid crystal device, the substrates are subjected to rubbing with a cloth comprising fiber of ca. 20 $\mu$m in diameter after patterning the electrodes thereon for partitioning the pixels, so that an alignment irregularity is liable to occur in one pixel or between adjacent pixels. Accordingly, for evaluation and development of such liquid crystal devices, it is important to evaluate a pretilt angle in a minute region of several $\mu$m to several tens $\mu$m in diameter and compare it with a designated value. Not only in such an active matrix-type liquid crystal device but also in a simple matrix-type liquid crystal device, it is useful to know the degree of alignment irregularity for improvement in alignment steps and finding of inferior products on a production line.

However, in the above-mentioned conventional optical anisotropy measurement apparatus 200, a beam (parallel light flux) is incident to a liquid crystal cell as it is, the irradiation region is considerably large (i.e., the incident beam A has a beam diameter of ca. 1 mm as described above). Moreover, the measurement region is deviated corresponding to the rotation of the liquid crystal cell 205 as described above. Accordingly, the measurement of pretilt angle in a minute region is impossible, so that it is difficult to detect a local irregularity of pretilt angle (alignment irregularity).

Further, not only in a liquid crystal cell, but also in measurement of optical anisotropy distribution of an object having a varying optical anisotropy in a particular direction, an accurate examination has been impossible because of a deviation in measurement region.

On the other hand, there has been also known a method of measuring an optical anisotropy of liquid crystal to determine a pretilt angle by the Senarmont method different from the crystal rotation method by using a conventional optical anisotropy measurement apparatus 210 as shown in FIG. 14 attached hereto.

Referring to FIG. 14, the optical anisotropy measurement apparatus 210 includes a He-Ne laser 201, a polarizer 202, an incident optical system 211, an outgoing optical system 212, a quarter wave plate 209, an analyzer 203 and a photodetector 204. A liquid crystal cell 205 as an object to be examined is disposed between the incident optical system 211 and the outgoing optical system 212. The liquid crystal cell 205 comprises a pair of glass substrates respectively having thereon alignment films (not shown) and a liquid crystal sealed between the alignment films. The liquid crystal cell 205 is supported rotatably about a rotation axis 208 extending in a direction perpendicular to a central axis of an incident beam A emitted from the He-Ne laser 201 (i.e., in a direction normal to the drawing). The analyzer 203 is supported rotatably about a rotation axis (not shown) extending parallel to the central axis of the incident beam A emitted from the laser 201.

Now, the principle of optical anisotropy measurement (principle of pretilt angle determination) for a liquid crystal layer 207 by the optical anisotropy measurement apparatus 210 will be described.

An incident beam A (laser beam, parallel light flux) emitted from the He-Ne laser 201 passes through the polarizer 202 to be transformed into linear polarized light and converged by the incident optical system 211 to enter the liquid crystal cell 205. The incident beam A having entered the liquid crystal cell 205 interacts with liquid crystal molecules therein to change its polarization state, i.e., to generally form elliptically polarized light and go out of the liquid crystal cell 205. The outgoing beam B emitted from the liquid crystal cell is converted into parallel light flux and passes though the quarter wave plate 209 and analyzer 203 to reach the photodetector 204.

When the liquid crystal cell 205 supported rotatably about the rotation axis 208 extending perpendicular to the central axis of the incident beam A (and vertical to the drawing) in the liquid crystal layer 207 is rotated, e.g., in a clockwise direction, the director of liquid crystal molecules (which is a unit vector representing the orientation direction of liquid crystal molecules) is changed relative to the electric field direction of the incident beam A entering the liquid crystal layer 207. Accordingly, corresponding to the rotation angle of the liquid crystal cell 205, the polarization state of the outgoing beam B going out of the liquid crystal cell 205 is changed.

In this instance, corresponding to the rotation angle of the liquid crystal cell 205, the analyzer 203 is rotated to detect an extinction azimuth of the outgoing beam B by the photodetector. More specifically, while the liquid crystal cell 205 is rotated, e.g., at a pitch of 0.5 deg., the liquid crystal cell 205 is once fixed at each rotation angle and the analyzer 203 is rotated to determine an extinction azimuth of the outgoing beam B, whereby a phase difference between ordinary rays and extraordinary rays having passed through the liquid crystal layer 207 can be measured.

The phase difference between ordinary rays and extraordinary rays transmitted through the liquid crystal layer 7 is plotted versus the rotation angle of the liquid crystal cell to obtain a characteristic curve. Based on the fact that the manner of change in phase difference between ordinary rays and extraordinary rays corresponding to the rotational change depends on the magnitude of pretilt angle, it is possible to determine a pretilt angle from the characteristic curve.

More specifically, a pretilt angle may be determined by comparing such a characteristic curve with calculated data based on the following equation (3):

$$\delta(\theta) = (2\pi d/\lambda)\left[n_o n_e (n^2(\alpha) - \sin^2\theta)^{1/2} / n^2(\alpha) - (n_o^2 - \sin^2\theta)^{1/2} - ((n_e^2 - n_o^2)/n^2(\alpha)) \cdot \sin\alpha \cdot \cos\alpha \cdot \sin\alpha\right], \quad (3)$$

wherein: phase difference between ordinary and extraordinary rays. $n_o$ and $n_e$: refractive indices for ordinary rays and extraordinary rays, respectively, of the liquid crystal, $\theta$: rotation angle of the liquid crystal cell 205, $\alpha$: pretilt angle, d: thickness of the liquid crystal layer 207, and $\lambda$: wavelength of the incident beam A.

In the above equation (3), $n_o$, $n_e$ and $\lambda$ are known values. A characteristic curve obtained by the Senarmont method ($\delta(\theta)$) (ordinary) versus $\theta$ (abscissa) makes a curve showing a single maximum of $\delta(\theta)$ at a certain value of angle $\theta$ (referred to herein as $\theta x$) which depends solely on $\alpha$ (while the magnitude of the maximum $\delta(\theta)$ depends on both $\alpha$ and d).

Accordingly, a pretilt angle $\alpha$ may be determined so as to provide $\theta x$ based on the equation (3) coinciding with the value $\theta x$ in the measured characteristic curve.

Incidentally similar optical anisotropy measurement as that described with reference to FIG. 14 may be possible even without the quarter wave plate 209, but a better measurement accuracy can be attained by using such a quarter wave plate 209.

As described above, the optical anisotropy measurement apparatus 210 allows the measurement of an optical anisotropy of a liquid crystal layer 207 based on the change in phase difference between ordinary rays and extraordinary rays of the outgoing beam B from the liquid crystal cell 205 caused by the interaction of the linearly polarized incident beam A and the liquid crystal molecules in the liquid crystal layer 207, and the determination of a pretilt angle based on the measured optical anisotropy.

The formerly described optical anisotropy measurement apparatus 200 and the optical anisotropy measurement apparatus 210 described now can be used as an apparatus for performing any of the crystal rotation method and the Senarmont method by adding the following modifications.

For example, if the analyzer 203 is fixed and no quarter wave plate 209 is used, an optical anisotropy measurement apparatus for the crystal rotation method can be attained On the other hand, if the analyzer 203 is rotatably disposed and the quarter wave plate 209 is used in order to provide an improved measurement accuracy, an optical anisotropy measurement apparatus for the Senarmont method can be attained.

Further, if the analyzer 203 is supported rotatably and easily fixably and the quarter wave plate 209 is disposed at a position movable onto an optical path of the outgoing beam B as desired, it is possible to constitute an optical anisotropy measurement apparatus which can be used for any of the crystal rotation method and the Senarmont method.

However, the above-mentioned optical anisotropy measurement apparatus 210 according to the Senarmont method is accompanied with similar problems as in the optical anisotropy measurement apparatus 200 according to the crystal rotation method as described above so that it has been impossible to detect a pretilt angle irregularity (change) at a spatial resolution of ca. 10 µm or smaller.

More specifically, a deviation e of measurement position occurs corresponding to the rotation of the liquid crystal cell 5 so that the measurement of pretilt angle at an identical region of the liquid crystal layer cannot be performed (see FIG. 13).

For the above reason, there has been proposed a method wherein a rotation angle position is determined so as to minimize the deviation e of measurement position and the liquid crystal cell is rotated about the rotation axis thus determined (K. Y. Han, et al., Jpn. J. Appl. Phys. Vol. 21 (1993) pp. L277–L279). This method is applicable to both of the crystal rotation method and the Senarmont method. A simple principle of the method is described with reference to FIG. 15. Referring to FIG. 15, if a rotation angle of a liquid crystal cell 206 (i.e., an incidence angle of a beam A incident to an incidence substrate 206a) is denoted by $\theta$, an angle of the incident beam A in the glass substrate 206 with respect to a normal to the glass substrate 206a is denoted by $\theta'$, a half of the thickness of the liquid crystal cell 205 is denoted by F, the refractive index of the glass substrate 206a is denoted by n, and a distance of the rotation axis 218 from the central position in the liquid crystal layer 207 is denoted by X, a deviation e in measurement position may be represented by the following formula (4):

$$e = (F-x)\tan\theta - F\tan\theta' \quad (4),$$

wherein $\sin\theta = n \cdot \sin\theta'$.

By obtaining a relationship between $\theta$ and x giving e=0, the optimum position of the rotation axis 218 can be determined.

According to this method, however, it is necessary to shift the position of the rotation axis 218 on the order of several µm corresponding to the rotation of the liquid crystal cell, so that a highly accurate and complex mechanism is required.

Accordingly, in an actual apparatus, the liquid crystal cell 205 is rotated about an appropriately determined rotation axis to obtain an approximate value of pretilt angle. Then, a range of rotation angle necessary for measurement is determined based on the approximate value of pretilt angle, and then the position of the rotation angle 218 is determined so as to provide a minimum deviation in measurement position in the range to effect the objective pretilt angle measurement. Accordingly, in actual measurement, the deviation in measurement position cannot be completely removed but remains on the order of 3–5 µm. Further, one measurement requires a considerable time.

For the above reason, this method is not suitable for detecting a pretilt angle irregularity in a minute region of the liquid crystal layer based on a spatial resolving power on the order of several µm.

Further, the optical anisotropy measurement according to the Senarmont method is accompanied with a problem that the pretilt angle determination can be performed only in a range of 0–ca. 13 deg. in case where the rotation angle of the liquid crystal cell 208 is, e.g., in the range of 0–60 deg.

Incidentally, in the optical anisotropy measurement apparatus 210 shown in FIG. 14, an incident optical system 211 is used to converge the incident beam A so as to allow a measurement at a minute region. In either of the crystal rotation method and the Senarmont method, an incident optical anisotropy as shown in FIG. 14 may be required to convert the incident beam A into a convergent beam (light flux) in order to measure an optical anisotropy at a minute region in a liquid crystal layer 207. However, the rotation of the liquid crystal cell 205 is accompanied with a change in incident angle with respect to the glass substrate 206a on the incidence side of the laser beam A. Then, as the rotation angle of the liquid crystal cell 205 is increased, there arise increased spherical aberration and astigmatism caused by influence of the glass substrate 206a, so that it has been impossible to converge the incident beam A at a minute region on the order of several µm.

The spherical aberration and astigmatism depend on factors, such as the F-number of the incident optical system 211 for converging the incident beam A into convergent light flux, the residual aberration of the optical system 211, the thickness of the incidence side glass substrate 206a and the rotation angle of the liquid crystal cell 205. In case where the glass substrate 206a has a thickness of 1 mm and a refractive index of 1.515, for example, when the incident beam A is to be converged by an optical system capable of converted diameter of 5 μm in air at a rotation angle of the liquid crystal cell 205 of 45 deg., the convergence is only possible down to ca. 7 μm in the axial direction of the rotation axis 208 principally due to spherical aberration and down to ca. 50 μm in a direction perpendicular to the rotation axis 208 principally due to astigmatism. More specifically, the spatial resolution is limited to ca. 7 μm in the rotation axis 208 direction and to ca. 50 μm in a direction normal thereto.

Further, in case where the incident beam A is to be converged by using an optical system capable of providing a converged beam diameter of 1 μm in air under identical conditions, the influence of astigmatism is increased, so that the converged diameter of the incident beam A largely depends on the determination of a focal point because a clear focal point cannot be determined because of the astigmatism. More specifically, at the time when the smallest converged diameter is provided in the rotation axis 208 direction, the spatial resolution amounts to ca. 60 μm in the rotation axis 208 direction and 230 μm in the direction normal thereto. On the other hand, at the time of providing the smallest converged diameter in the direction normal to the rotation axis 208, the spatial resolution amounts to ca. 100 μm in the rotation axis 208 direction and ca. 100 μm in the direction normal thereto.

Further, in case where the incident beam A is tried to be converged by using an optical system capable of providing converged beam diameter of 20 μm in air under identical conditions, the resultant spatial resolution amounts to ca. 20 μm in the rotation axis 208 direction and ca. 45 μm in the direction normal thereto.

As described above, if an optical system having a small F-number (larger N.A. (numerical aperture)) is used to converge the incident beam A into a smaller diameter, there results a larger influence of astigmatism due to the rotation of the glass substrate 206a. Accordingly even if convergence of the incident beam A is attempted using an input optical system as used in a conventional optical anisotropy measurement apparatus 210 according to the Senarmont method as shown in FIG. 14 (e.g., even if the incident beam A is to be converged is attempted using an optical system capable of providing a converged diameter down to several μm in air), it has been impossible to measure a pretilt angle at a small region having a diameter of 10 μm or smaller in the liquid crystal layer 207.

SUMMARY OF THE INVENTION

Accordingly, an object of the present invention is to provide an optical anisotropy measurement apparatus capable of measuring an optical anisotropy at an identical region of an rotating object to be examined by disposing a prescribed transparent member having a curved surface and a flat surface in close contact with the object to be examined, and also an optical anisotropy measurement method using the apparatus.

Another object of the present invention is to provide an optical anisotropy measurement apparatus capable of measuring an optical anisotropy at a small region of an object to be examined by disposing a prescribed incident optical system between a light source and the object to be examined, and an optical anisotropy measurement method using the apparatus.

A further object of the present invention is to provide an optical anisotropy measurement apparatus capable of measuring an optical anisotropy at a desired region of an object to be examined by disposing an incident optical system movably or by disposing a stop means, and an optical anisotropy measurement method using the apparatus.

A still further object of the present invention is to provide an optical anisotropy measurement apparatus capable of obviating deterioration in measurement accuracy even if an analyzer having an incident angle-dependence is used, by disposing a prescribed first exit optical system between an object to be examined and the analyzer to provide a parallel beam (light flux) incident to the analyzer, and an optical anisotropy measurement method using the apparatus.

Another object of the present invention is to provide an optical anisotropy measurement apparatus having an excellent detection efficiency by disposing a prescribed exit optical system between an object to be examined and a photodetector to provide an increased light quantity incident to the photodetector, and an optical anisotropy measurement method using the apparatus.

Another object of the present invention is to provide an optical anisotropy measurement apparatus capable of measuring a pretilt angle of a liquid crystal contained in a liquid crystal cell as an object to be examined actually incorporated in a liquid crystal device, and an optical anisotropy measurement method using the apparatus.

A further object of the present invention is to provide a process for producing a liquid crystal device while using the above mentioned apparatus and method for measuring an optical anisotropy of a liquid crystal in a liquid crystal device to determine a pretilt angle, thereby improving the liquid crystal alignment step, improving the liquid crystal device production steps and effectively finding inferior products on a production line.

According to the present invention, there is provided an optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector; said optical anisotropy measurement apparatus further including:

a supporting member for supporting the object to be examined rotatably about a rotation axis extending perpendicular to the straight line, a polarizer positioned between the light source and the object to be examined, an analyzer positioned between the object to be examined and the photodetector, and an optical member disposed between the light source and the object to be examined so as to cause the beam to pass through an intersection of said straight line and said rotation axis.

In a preferred embodiment, the above-mentioned optical member may be constituted as a pair of transparent members each having a curved surface and a flat surface disposed so as to sandwich the object to be examined with their opposing flat surfaces.

According to another aspect of the present invention, there is provided an optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector; said optical anisotropy measurement apparatus further including:

a supporting member for supporting the object to be examined rotatably about a first rotation axis extending perpendicular to the straight line, a polarizer positioned between the light source and the object to be examined, an analyzer positioned between the object to be examined and the photodetector, and a first flat transparent sheet member positioned between the light source and the object to be examined and supported rotatably about a second rotation axis extending parallel to said first rotation axis.

According to a further aspect of the present invention, there is provided a method for measuring an optical anisotropy of an object to be examined by using any of the above-mentioned apparatus.

In a preferred embodiment, the object to be examined comprises a liquid crystal cell containing a liquid crystal disposed between a pair of substrates.

According to still another aspect of the present invention, there is provided a process for producing a liquid crystal device, including a step of measuring an optical anisotropy of a liquid crystal by the above-mentioned optical anisotropy measurement method.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 1 to 10 are schematic illustrations of first to tenth embodiments, respectively, of the optical anisotropy measurement apparatus according to the invention.

FIG. 11 is a schematic illustration of a known optical anisotropy measurement apparatus according to the crystal rotation method.

FIG. 14 is a schematic illustration of a known optical anisotropy measurement apparatus according to the Senarmont method.

FIG. 15 is a view for illustrating a principle for reducing a deviation in measurement position in a known optical anisotropy measurement apparatus and a problem accompanying the apparatus.

DESCRIPTION OF THE PREFERRED EMBODIMENTS

Figure 1:
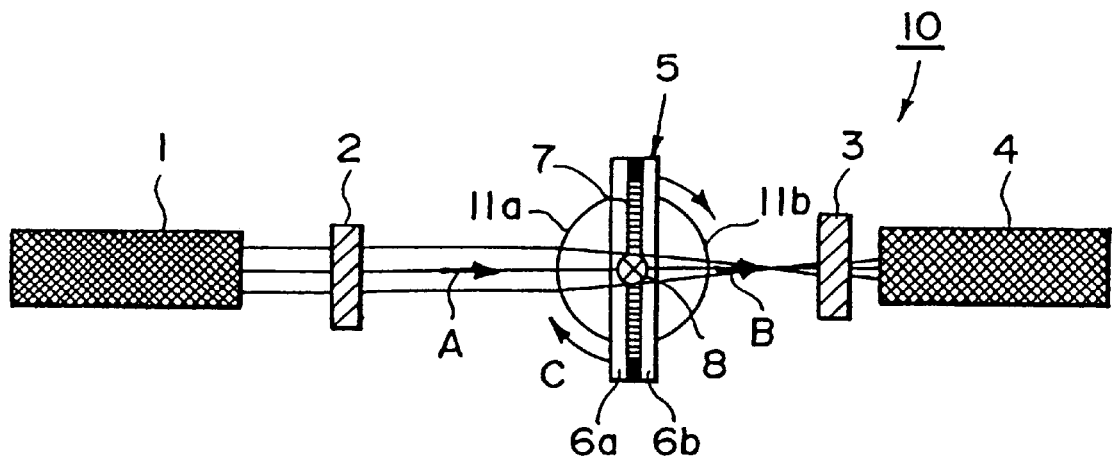

FIG. 1 is a schematic illustration of an optical anisotropy measurement apparatus according to the present invention. Referring to FIG. 1, an optical anisotropy measurement apparatus includes 10 includes a He-Ne laser (light source) 1, a polarizer 2, an analyzer 3 and a photodetector 4, and a liquid crystal cell 5' being an object to be examined, is disposed between the polarizer 2 and the analyzer 3.

The liquid crystal cell 5 comprises a pair of glass substrates 6a and 6b respectively having alignment films (not shown) on their inner sides and a liquid crystal layer 7 disposed between the alignment films. The liquid crystal cell 5 is supported by a supporting member (not shown) rotatably about a rotation axis 208 extending in a direction perpendicular to an optical axis (central axis) of an incident beam A (laser beam) emitted rom the He-Ne laser 1 and is rotated in a direction of arrow (clockwise) or a direction (counterclockwise) opposite thereto by a rotation drive apparatus (not shown). In case where at least one of the alignment films is subjected to a uniaxial aligning treatment, the uniaxial alignment axis may be disposed in a direction perpendicular to the rotation axis 8.

The polarizer 2, the analyzer 3 and the photodetector 5 are disposed on a central axis of the incident beam emitted from the He-Ne laser 1.

Spherical segment glasses 11a and 11b are attached to the polarizer side of the incidence-side glass substrate 6a and the analyzer side of the exit-side glass substrate 6b, respectively, via a refractive index-matching liquid (not shown). The spherical segment glasses 11a and 11b are respectively designed to have a curvature center coinciding with an intersection of a rotation center (rotation axis 8) of the liquid crystal cell 5 and the central axis of the incident beam A.

The spherical segment glasses 11a and 11b respectively have a curvature center within the liquid crystal layer so that they are not hemispherical in a strict sense but can be approximately regarded as hemispherical because the liquid crystal cell 5 has a small thickness.

The spherical segment glasses 11a and 11b are formed of a glass material having a refractive index almost equal to those of the glass substrates 6a and 6b of the liquid crystal cell 5, and also the refractive index-matching liquid comprises a liquid having a refractive index almost equal to those of the glass substrates 6a and 6b. More specifically an index-matching oil used in a wet-type microscope may be used for the refractive index-matching liquid.

Herein, almost equal refractive indices mean such a closeness of refractive index that total reflection is not caused at boundaries between the spherical segment glasses 11a, 11b and the refractive index-matching liquid or at boundaries between the matching liquid and the glass substrates 6a, 6b, even when the liquid crystal cell 5 is rotated during the measurement, and may be determined depending on the incident angle. More specifically, the refractive index-matching liquid has a refractive index which differs from those of the spherical segment glasses 11a, 11b and the glass substrates 6a, 6b, respectively, within a range of ±0.05.

The glass substrates 6a, 6b may preferably comprise a transparent or almost transparent (preferably, transparent) glass material free from optical anisotropy. Incidentally, the spherical segment glasses 11a, 11b and the glass substrates 6a, 6b need not be composed of glass but can alternatively comprise a transparent or almost transparent member of, e.g., a plastic material.

The light source 1 can be an Ar laser, a semiconductor laser or a beam emission apparatus other than a laser, such as a thermal radiation source, in addition to the He-Ne laser but may preferably comprise an apparatus emitting a beam or light flux that can be condensed. The light source 1 may preferably be one free from aberration such as astigmatism and capable of emitting monochromatic light free from chromatic aberration.

The photodetector 4 may comprise an optical power meter, a photomultiplier, etc., but may preferably be one of a high sensitivity.

In the case of measuring an optical anisotropy according to the crystal rotation method, the analyzer 3 is disposed to have a polarization direction which is parallel or perpendicular to that of the polarizer 2 (i.e., a parallel nicol or cross nicol position). On the other hand, in the case of measuring an optical anisotropy according to the Senarmont method, the analyzer 3 is disposed rotatably about a rotation axis (not shown) extending parallel to the central axis of the incident beam A. Further, in the case of the Senarmont method, it is preferred to dispose a quarter wave plate (not shown) between the spherical segment glass 11b and the analyzer 3.

All the embodiments described herein including the above-mentioned first embodiment and those appearing hereinafter may be used for measurement according to any of the crystal rotation method and the Senarmont method by adding the modifications described in the preceding paragraph. Further, if the analyzer 3 is supported rotatably and easily fixably and a quarter wave plate is disposed at a position movable onto an optical path of the outgoing beam B only when required, it is possible to constitute an optical anisotropy measurement apparatus which can be used for any of the crystal rotation method and the Senarmont method.

Now, an optical anisotropy measurement method (method of determining a pretilt angle) according to the crystal rotation method by using the optical anisotropy measurement 10 will be described.

Incident beam A emitted from the He-Ne laser apparatus 1 passes through the polarizer 2 to be linearly polarized light and enters the spherical segment glass 11a. By entering the spherical segment glass 11a, the incident beam A is somewhat converged to be incident to the liquid crystal cell 5, where the beam A interacts with the liquid crystal molecules in the liquid crystal layer 7 to leave the liquid crystal cell 5. As described above, the spherical segment glasses 11a, 11b intimately contacts the liquid crystal cell 5 via the refractive index-matching liquid, and these members and liquid have almost equal refractive indices, the incident beam A enters the liquid crystal cell 5 without refraction. Further, the spherical segment glasses 11a, 11b respectively have a curvature center on the rotation axis 8, so that no change in measurement position is caused even when the liquid crystal cell 5 is rotated (while some enlargement of the measurement region is caused as the rotation angle of the liquid crystal cell 5 is increased).

Then, the outgoing beam B leaving the spherical segment glass 11b passes through the analyzer 3 having a polarization direction parallel or perpendicular to that of the polarizer 2 to reach the photodetector 4.

Figure 12:
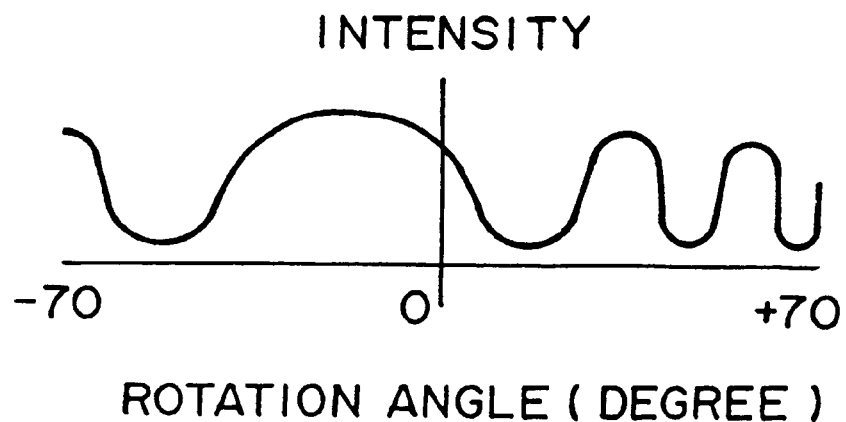
FIG. 12 is a graph showing an example of measured optical anisotropy pattern obtained by using such an optical anisotropy measurement apparatus.
Figure 13:
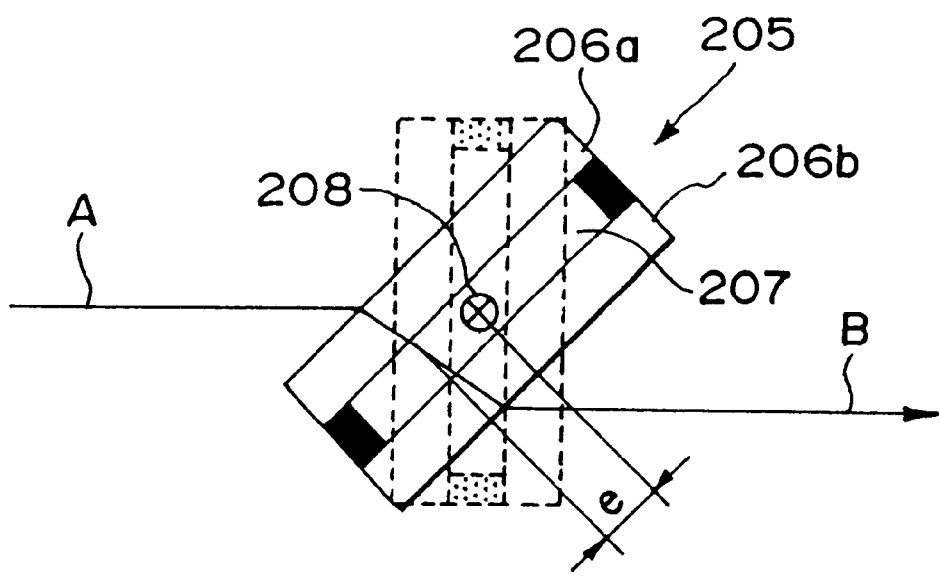
FIG. 13 is a view for illustrating a problem involved in the known optical anisotropy measurement apparatus.

In this instance, the liquid crystal cell 5 supported about the rotation axis 8 is rotated in the arrow direction or the direction opposite thereto by a rotation driver, whereby the polarization state of the outgoing beam B having passed through the liquid crystal cell varies corresponding to the rotation axis of the liquid crystal cell. As the light quantity passing through the analyzer 3 of the outgoing beam B varies depending on the polarization state of the outgoing beam B, a characteristic curve as shown in FIG. 12, for example, may be obtained by plotting the outputs of the photodetector 4 versus the rotation axis of the liquid crystal cell 5. A pretilt angle may be determined from the characteristic curve in the manner described with reference to FIG. 11.

According to this embodiment, the measurement may be performed at an identical region without deviation even when the liquid crystal cell 5 is rotated, a pretilt angle at the measurement region can be accurately determined.

Now, a second embodiment of the present invention will be described with reference to FIG. 2, wherein members identical to those in FIG. 1 are denoted by identical reference numerals, and the description thereof may be omitted.

Figure 2:
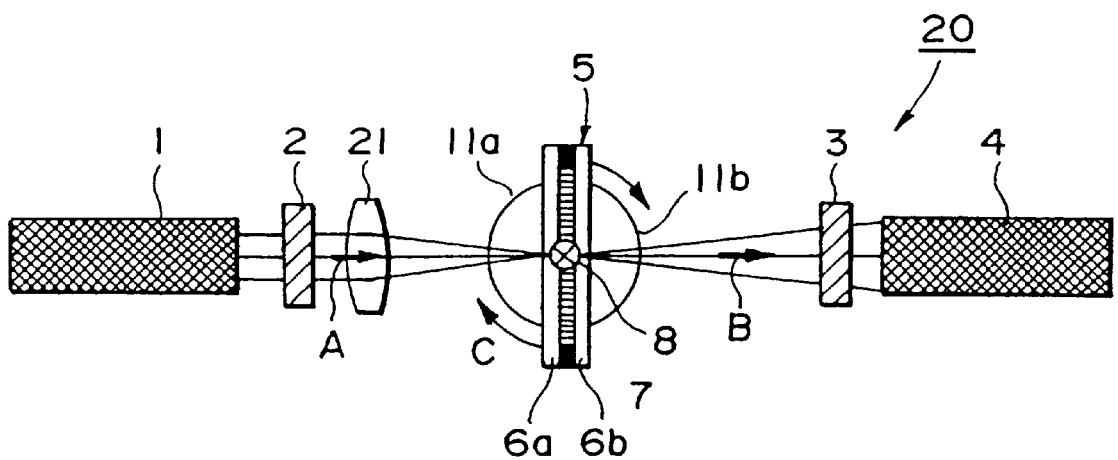

Referring to FIG. 2, an optical anisotropy measurement apparatus 20 according to this embodiment includes a convex lens (an incident optical system having a positive power) 21 is disposed between the polarizer 2 and the spherical segment glass 11a, so that an incident beam A (parallel light flux or beam) emitted from the He-Ne laser is converted into a convergent beam (convergent spherical wave). In this embodiment, the convergent flux is designed to have a curvature center coinciding with the curvature center of the spherical segment glass 11a. For this reason, the incident beam A after the conversion by the convex lens is focused at a measurement region without refraction at the spherical surface of the spherical segment glass 11a.

According to this embodiment, a measurement at an identical region (while the size thereof may be changed slightly) is possible even when the liquid crystal cell 5 is rotated, a pretilt angle at the region can be determined accurately. Further, according to this embodiment, the incident beam A is converged by the convex lens 21 to be focused at the rotation center of the liquid crystal cell 5, so that a measurement at a minute region becomes possible. Further, as the spherical segment glass 11a is present, it becomes possible to remove the spherical aberration and astigmatism which have been problematic heretofore. Accordingly, it is possible to effect a measurement at a remarkably improved resolving power, e.g., as to allow the detection of a pretilt angle irregularity in one pixel, so that information effective for improving the steps for producing liquid crystal devices and the performances of a liquid crystal device per se can be obtained.

Incidentally, the beam diameter at the convergent point, i.e., beam diameter at the measurement surface, is principally determined by the N.A. (numerical aperture) of the convex lens 21. Accordingly, if the N.A. of the convex lens 21 is increased, the measurement region can be decreased in size. In this embodiment, the parallel flux beam having a diameter of ca. 1 mm issued from the He-Ne laser is converged to a diameter of ca. 30 μm. Now, if the convex lens 21 is completely free from aberration, it is possible to converge the beam down to the diffraction limit. On the other hand, when such a convex lens 21 is used, the incident beam becomes a convergent light flux incident to the liquid crystal boundary so that the incident angle to the liquid crystal boundary is accompanied with a spreading, thus being liable to result in a slightly worse measurement accuracy. The degree of worsening of the measurement accuracy is more pronounced at a larger N.A. However, convergent light flux is approximate to parallel light flux, the spreading of the incident angle is not so serious as to deteriorate the measurement accuracy.

Now, a third embodiment of the present invention will be described with reference to FIG. 3, wherein members identical to those in FIG. 1 are denoted by identical reference numerals, and the description thereof may be omitted.

Figure 3:
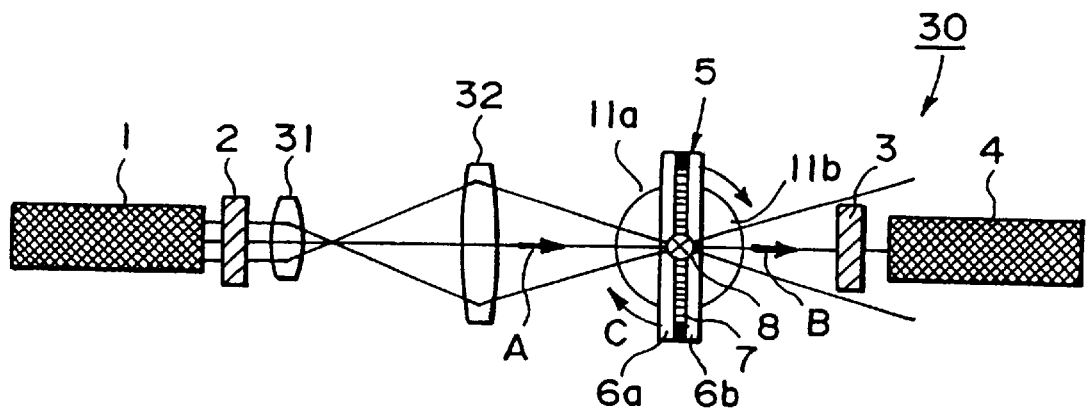

Referring to FIG. 3, an optical anisotropy measurement apparatus 30 according to this embodiment includes two convex lenses 31 and 32 between the polarizer 2 and the spherical segment glass 11a so as to form an incident optical system having a positive power. Of these, the convex lens 31 disposed closer to the polarizer 2 is designed to once converge the incident beam A (parallel light flux) into convergent light flux (convergent spherical wave) and then convert it into a divergent beam having an enlarged beam diameter to be incident to the other convex lens 32. The convex lens 32 is designed to convert the incident divergent beam again into a convergent beam (convergent spherical wave). Accordingly, in this embodiment, the two convex lenses 31 and 32 are used to provide a large N.A. and reduce the convergent beam entering the liquid crystal boundary to a beam diameter of several $\mu$m. Similarly as in the second embodiment, the convergent beam is designed to have a curvature center coinciding with the curvature center of the spherical segment glass 11a.

According to this embodiment, it is possible to provide a still larger N.A. and provide the convergent beam incident to the liquid crystal boundary with a beam diameter of several $\mu$m. Accordingly, it is possible to measure a pretilt angle at a region even smaller than in the second embodiment. Further, similarly as in the previous embodiments, it is possible to effect a measurement at an identical measurement region, the pretilt angle at the region can be measured accurately.

In the above-mentioned second and third embodiments, the incident optical system (convex lens 21 or convex lenses 31 and 32) is disposed so that the incident beam is converged at the rotation center of the liquid crystal cell 6, but this is not necessary. For example, it is possible to dispose the incident optical system movably in an optical axis direction so that the convergent point can be shifted. It is also possible to dispose a single or plural circular apertures (stop means) between the incident optical system and the spherical segment glass so as to cause a change in effective N.A., whereby the size of measurement region can be changed and it becomes possible to obtain information, e.g., one as to from what size of region, the irregularity in pretilt angle becomes pronounced. In this instance, the aperture size can be made variable.

A fourth embodiment of the present invention will now be described with reference to FIG. 4, wherein members identical to those in FIG. 3 are denoted by identical reference numerals and the description thereof may be omitted.

Figure 4:
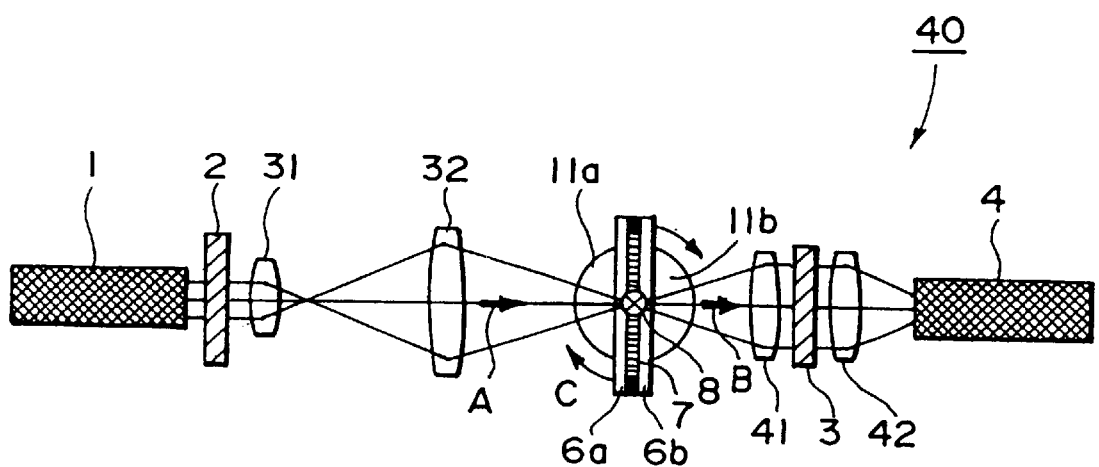

Referring to FIG. 4, an optical anisotropy measurement apparatus 40 according to this embodiment has a structure similar to that of the above-described optical anisotropy measurement apparatus 30 shown in FIG. 3 but is different from the latter in that it further includes a convex lens (first exit optical system) 41 between the spherical segment lens 11b and the analyzer 3, and also a convex lens (second exit optical system) 42 between the analyzer 3 and the photodetector 4. By these convex lenses 41, 42 (exit optical system), the outgoing beam B in the form of a divergent light flux leaving the spherical segment glass 11b is converted into a parallel flux to be incident to the analyzer 3 and the beam having passed through the analyzer 3 is converted into a convergent flux to be incident to the photodetector 4. In this embodiment, the exit optical systems 41, 42 are each composed of a single lens, but each optical system can comprise plural lenses.

An analyzer 3 composed of a polarizing element such as a Glan-Thompson prism, generally has an incident angle-dependence. More specifically, when a beam entering the analyzer 3 comprises various angle components, including those providing an incident angle to the analyzer exceeding a tolerable range (ca. ±7 degrees in the case of a Glan-Thompson prism), the performance of the analyzer 3 is deteriorated, e.g., so as to allow the transmission of a polarization component having a polarization perpendicular to that of the analyzer 3, thus resulting in an inferior measurement accuracy. According to this embodiment, however, the beam entering the analyzer 4 has been transformed into parallel light flux by the optical system 41, so that such an inferior measurement accuracy can be obviated. Further, the parallel light flux (beam) having passed through the analyzer 3 is converged by the optical system 42 before entering the photodetector 4, so that the light quantity entering the photodetector 4 is increased to provide an improved detecting efficiency.

Also in this embodiment, similar effects as in the preceding embodiments can be attained. Thus, regardless of the rotation of the liquid crystal cell 5, a pretilt angle at an identical region is measured so that the pretilt angle can be determined accurately to provide an improved measurement accuracy. Further, a measurement at a minute region becomes possible so that information effective for improving the liquid crystal device production process, etc., may be obtained.

Next, a fifth embodiment of the present invention will be described with reference to FIG. 5, which is an enlarged view of a part surrounding a liquid crystal cell in an optical anisotropy measurement apparatus 50 according to this embodiment.

In the apparatus 50 according to this embodiment, the spherical segment glasses 11a, 11b are respectively composed of spherical segment portions 51a, 51b and flat sheet portions 52a, 52b formed continuously to the spherical segment portions 51a, 51b. The flat sheet portions 52a, 52b are coated with refractive index-matching liquids 54. The upper and lower ends of the liquid crystal cell 5 are set in position by gripping with liquid crystal cell holders 53, 55 each having an almost "U"-shaped cross-section. Surrounding the liquid crystal cell holders 53, 55, spherical segment glass holders 56, 57 also having almost "U"-shaped cross-sections are disposed to grip the spherical segment glasses 11a, 11b. According to these holders 53, 55 and 56, 57, the liquid crystal cell 5 is sandwiched by the spherical segment glasses 11a and 11b. These holders 53, 55 and 56, 57 are supported rotatably about the rotation axis 8 and rotated by a drive means (not shown). Further, the liquid crystal cell holders 53, 55 are supported movably in two dimensional directions (an up-and-down direction on the drawing and a direction normal to the drawing sheet) by a feeding mechanism (not shown), so that the liquid crystal cell position can be moved at a pitch of several $\mu$m relative to the spherical segment glasses 11a, 11b.

The description of the members not shown in FIG. 5 of this embodiment is omitted, but various optical systems used in the preceding embodiments of the optical anisotropy measurement apparatus can be applied to the optical alignment measurement apparatus 50 according to this embodiment.

According to this embodiment, a pretilt angle can be determined at a desired region of a liquid crystal cell, so that information useful for improving the liquid crystal device production process, etc., can be obtained.

Now, a sixth embodiment of the present invention will be described with reference to FIG. 6, wherein members identical to those in FIG. 1 are denoted by identical reference numerals, and the description thereof may be omitted.

An optical anisotropy measurement apparatus 60 according to this embodiment is an apparatus for effecting an optical anisotropy measurement according to the Senarmont method, and includes a quarter wave plate 9 on the object to be examined-side of the analyzer 3. Further, the analyzer 3 is rotatably about a rotation axis extending parallel to the incident beam A. However, this apparatus 60 can be used for an optical anisotropy measurement according to the crystal rotation method by removing the quarter wave plate 9 and fixing the analyzer 3. Further, the apparatus 60 includes an incident optical system 61 for converging the incident beam A between the analyzer 2 and the incidence-side spherical segment 11a.

The incident optical system 61 may preferably converge the beam emitted from the He-Ne laser to provide a converged beam diameter of 1–20 $\mu$m. In a specific example, the incident optical system 61 may be constituted to provide a convergent beam with an F-number of 7.44.

In such a specific example, where the liquid crystal layer has a thickness of 1 $\mu$m and the incident beam A has a wave length of 0.6328 $\mu$m, the incident beam A may be converged to a beam diameter of ca. 6 $\mu$m corresponding to a measurement region size of 6.0 $\mu$m in a direction parallel to the rotation axis 8 and ca. 9.0 $\mu$m in a direction perpendicular to the rotation axis.

Under identical conditions, if the F-number is 1.24, the incident beam A may be converged to a beam diameter of ca. 1 $\mu$m corresponding to a measurement region size of 1.2 $\mu$m in a direction parallel to the rotation axis 8 and ca. 2.7 $\mu$m in a direction perpendicular to the rotation axis.

Further, by using an Ar laser as a light source in place of the He-Ne laser 1, the measurement region size can be further reduced.

Incidentally, the F-number of a converged beam may be expressed by f/d, if the incident beam A entering a lens closest to the spherical segment glass 11a has a beam diameter d and the lens has a focal length f. More generally, the F-number of a lens or a group of lenses having a beam-converging function may be expressed by $f_0/\phi$, if a beam passing through a pupil plane has a diameter $\phi$ and the focal length is $f_0$.

The incident optical system used in the present invention may preferably be one capable of converging an incident beam A into a converged beam having an F-number of at most $3\pi/2\lambda$ wherein $\lambda$ denotes a wavelength ($\mu$m) of the incident beam A. A smaller F-number allows a larger degree of convergence of the incident beam A, but too large a convergence angle restricts the range allowed for rotation of the liquid crystal cell 5, so that it is preferred to use an incident optical system providing a converged beam with an F-number in a range of $\pi/5\lambda$ to $3\pi/2\lambda$.

The optical anisotropy measurement apparatus 60 according to this embodiment further includes a first exit optical system 62 between the exit-side spherical segment glass 11b and the quarter wave plate 9 so as to convert the outgoing beam B entering the analyzer 3 into a parallel beam (parallel light flux).

The apparatus 60 in this embodiment includes the incident optical system 61 composed of three convex lenses and the exit optical system 62 composed of a single convex lens. This is however not limitative.

In a manner similar to the first embodiment, the spherical segment glasses 11a, 11b intimately contact the glass substrates 6a, 6b of the liquid crystal cell 5 via a refractive index-watching liquid.

Now, an optical anisotropy measurement method (method of determining a pretilt angle) according to the Senarmont method by using the optical anisotropy measurement apparatus 60 will be described.

Incident beam A emitted from the He-Ne laser apparatus 1 passing through the polarizer 2 is converged by the incident optical system 61 and passes through the spherical segment to enter the liquid crystal cell 5. The incident beam A incident to the liquid crystal cell 5 interacts with liquid crystal molecules in the liquid crystal layer 7 to change its polarization state and generally form elliptically polarized light to leave the liquid crystal cell 5. As described above, the spherical segment glasses 11a, 11b intimately contact the liquid crystal cell 5 via a refractive index-matching liquid, and the refractive index-matching liquid has a refractive index almost equal to those of the spherical segment glasses 11a, 11b and the incident beam A enters the liquid crystal cell 5 without refraction. Further, the spherical segment glasses 11a, 11b have a curvature center on the rotation axis 8, so that the measurement region does not change even if the liquid crystal cell 5 is rotated (while the size of the measurement region somewhat varies).

The outgoing beam B leaving the liquid crystal cell 5 passes through the spherical segment glass 11b, becomes a parallel beam by the exit optical system 62 and passes through the quarter wave plate 9 and the analyzer 3 to reach the photodetector 4.

When the liquid crystal cell 5 supported rotatably about the rotation axis 8 extending in a direction perpendicular to the central axis of the incident beam A (and normal to the drawing) is rotated, e.g., in a clockwise direction as indicated by arrows, the director of liquid crystal molecules (which is a unit vector representing the orientation of liquid crystal molecules) in the liquid crystal layer 7 is changed relative to the electric field vector direction of the incident beam A. Accordingly, corresponding to the rotation angle of the liquid crystal cell 5, the polarization state of the outgoing beam B is changed. In this instance, corresponding to the rotation angle of the liquid crystal cell 5, the analyzer 3 is rotated to detect an extinction azimuth to measure a phase difference between ordinary rays and extraordinary rays having passed the liquid crystal layer 7. The phase difference values are plotted versus the rotation axis to obtain a characteristic curve, from which the pretilt angle of liquid crystal molecules in the liquid crystal layer 7 is determined in the manner described hereinbefore.

The optical anisotropy measurement apparatus 60 according to this etbodiment differs from the known optical anisotropy measurement apparatus in that it includes the spherical segment glass 11a, 11b to allow a measurement at an identical region even when the liquid crystal cell 5 is rotated during the measurement. Further, as the spherical aberration and the astigmatism have been removed, the measurement may be effected at a small region.

Further, while the optical anisotropy measurement according to the Senarmont method using a known optical anisotropy measurement apparatus has been accompanied with a problem that the pretilt angle determination can be performed only in a range of 0–13 deg. e.g., in case when the liquid crystal cell rotation angle is 0–60 deg., it is possible to measure the pretilt angle in a range of 0–18 deg. corresponding to the same rotation angle range when the optical anisotropy measurement apparatus 60 according to this embodiment is used.

Figure 6:
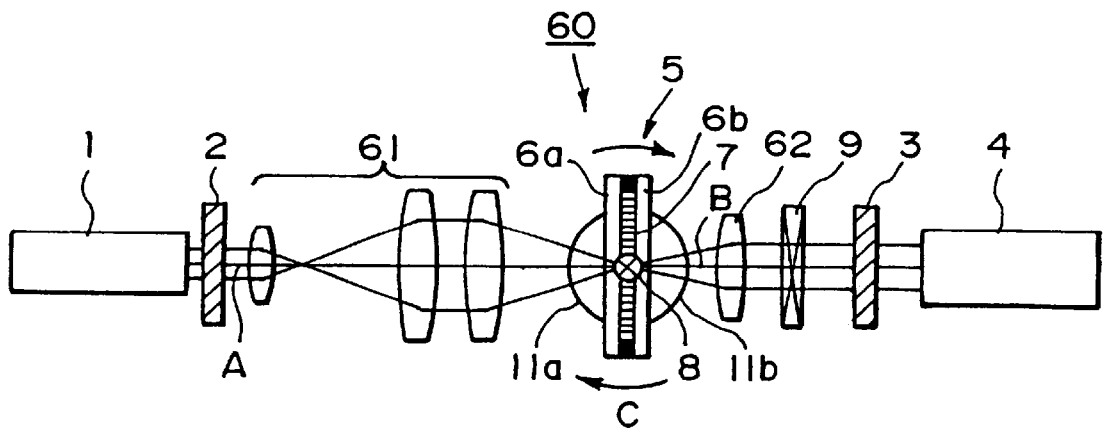

Now, a seventh embodiment of the present invention will be described with reference to FIG. 7, wherein members identical to those in FIG. 6 are denoted by identical reference numerals, and the description thereof may be omitted.

Figure 7:
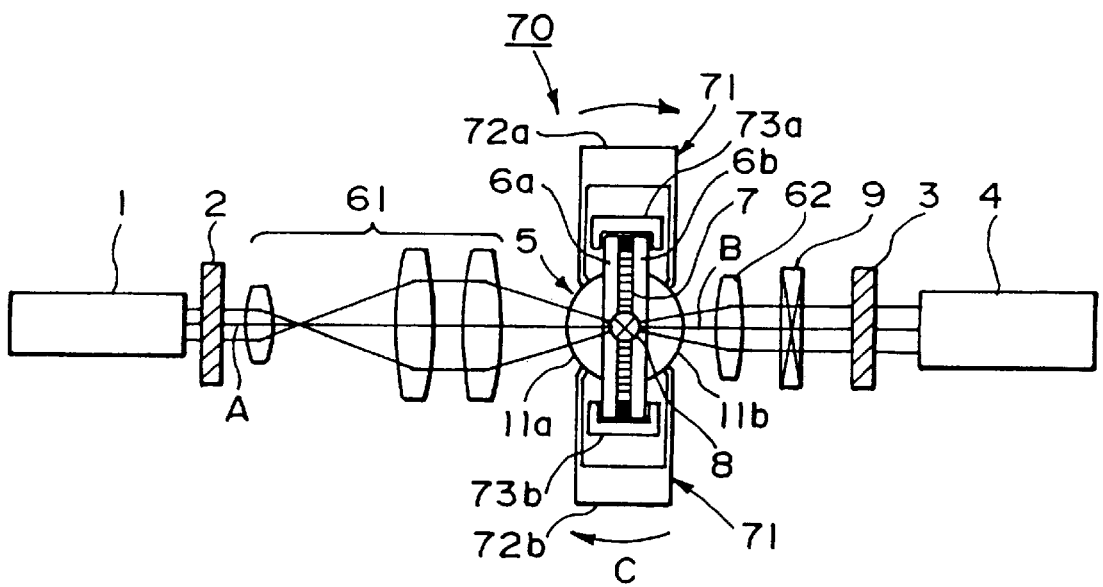

Referring to FIG. 7, an optical anisotropy measurement apparatus 70 according to this embodiment includes, liquid crystal holders 73a, 73b and a spherical segment glass holder 71 similar to those used in the optical anisotropy measurement apparatus 50 shown in FIG. 5 in addition to the structure of the optical anisotropy measurement apparatus 60 shown in FIG. 6. These holders 71, 73a and 73b have similar functions as the corresponding holders in the optical anisotropy measurement apparatus 50, but the holder 71 is designed to grip the spherical surfaces of the spherical segment glasses 11a, 11b, so that the spherical segment glasses 11a, 11b need not be provided with flat sheet portions. The apparatus 60 is constituted to be suitable for use in optical anisotropy measurement according to the Senarmont method.

Now, an eighth embodiment of the present invention will be described with reference to FIG. 8, wherein members identical to those in FIG. 1 are denoted by identical reference numerals, and the description thereof may be omitted.

Figure 8:
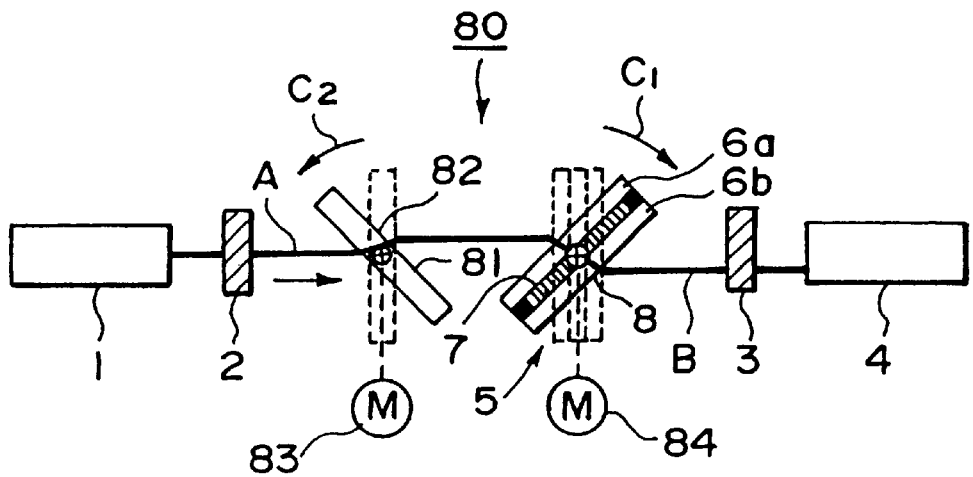

Referring to FIG. 8, an optical anisotropy measurement apparatus 80 according to this embodiment includes a flat sheet glass 81 between the polarizer 2 and the liquid crystal cell 5 as an object to be examined.

The flat sheet glass 81 is composed of a glass material having a refractive index and a thickness respectively identical to those of the incidence-side glass substrate 6a of the liquid crystal cell 5. Further, the flat sheet glass 81 is supported by a rotation axis 82 extending in a direction perpendicular to the central axis of the incident beam A and rotated by a rotational driver 83 connected to the rotation axis 82.

The liquid crystal cell 5 is supported by a rotation axis 8 extending in a direction perpendicular to the central axis of the incident beam A and rotated by a rotation driver 84.

The rotation driver 83 is controlled to rotate the flat sheet glass 81 at an equal angular velocity and in an opposite rotational direction direction (e.g., C2-direction) with respect to the rotation (e.g., in a C1-direction) of the liquid crystal cell 5 driven under control by the rotation driver 84.

In the optical anisotropy measurement apparatus 80 according to this embodiment, the optical anisotropy of a liquid crystal can be measured always at an identical region to determine a pretilt angle even if the liquid crystal cell 5 is rotated because of the rotation control of the flat sheet glass 81 in the above-described manner.

More specifically, an incident beam A is once caused to have a parallelly shifted optical path due to refraction at the time of entrance to and exit from the flat sheet glass 81, and then enters the glass substrate 6a of the liquid crystal cell 5 to cause a compensational refraction, thereby entering the liquid crystal layer 7 along a line in alignment with the extension of the original light path of the incident beam A (as emitted from the He-Ne laser 1).

As described above, according to the optical anisotropy measurement apparatus 80 of this embodiment, the optical anisotropy of the liquid crystal layer 7 can be measured accurately while canceling the deviation in measurement region due to the rotation of the liquid crystal cell 5.

Now, a ninth embodiment of the present invention will be described with reference to FIG. 9, wherein members identical to those in FIG. 8 are denoted by identical reference numerals, and the description thereof may be omitted.

Figure 9:
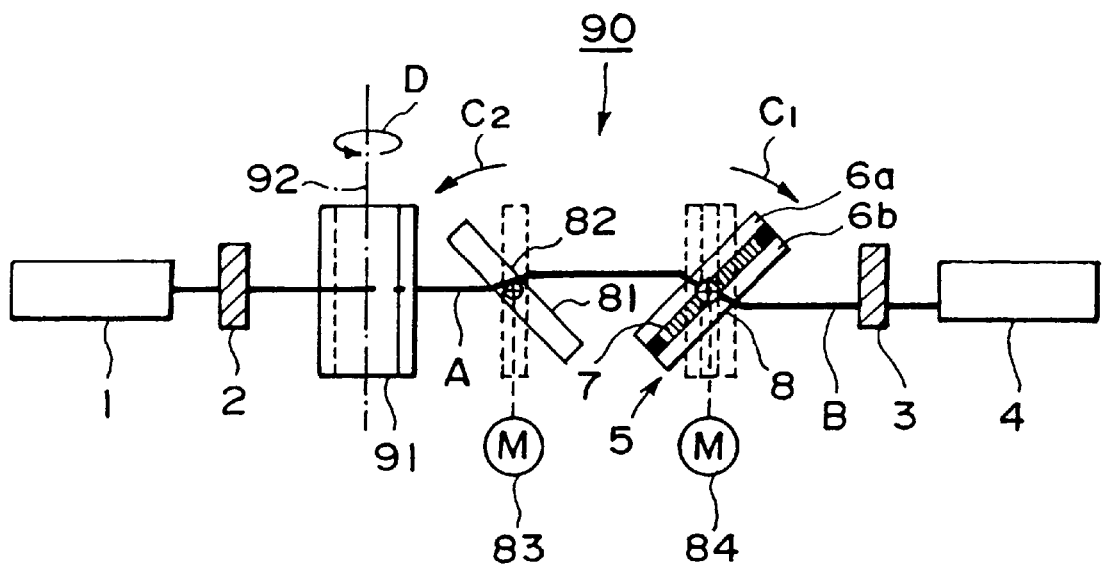

Referring to FIG. 9, an optical anisotropy measurement apparatus 90 according to this embodiment includes a second flat sheet glass 91 on an optical axis of the incident beam A between the polarizer 2 and the liquid crystal cell 5, so that the sheet glass 91 is supported rotatably about a rotation axis 92 extending in a direction perpendicular to the central axis of the incident beam A and perpendicular to the rotation axis 8 of the liquid crystal cell 5. The other arrangements are similar to those in the above-mentioned optical anisotropy measurement apparatus 80.

The second flat sheet glass 91 is rotated about the rotation axis 92, e.g., in the direction of an arrow D, under the control of a rotation driven (not shown).

When the second flat sheet glass 91 is rotated, the incident beam A emitted from the He-Ne laser 1 is refracted within the second flat sheet glass 91 to cause a parallel shift of optical path. As a result, the incident beam A is caused to enter the liquid crystal cell 5 at a desired position shifted along the rotation axis 8 of the liquid crystal cell.

For example, in case where the second flat sheet glass 91 has a refractive index of 1.5 and a thickness of 4.5 mm and where the rotation angle of the second flat sheet glass 91 is taken at 0 deg. when the beam A is incident to the sheet glass perpendicularly, the shift of measurement position at the liquid crystal cell 5 is ca. 1 mm at a rotation angle of 30 deg., ca. 2 mm at 40 deg. and ca. 3 mm at 52 deg., respectively of the second flat sheet glass 91.

Incidentally, in FIG. 9, the second flat sheet glass 91 is disposed between the polarizer 2 and the flat sheet glass 81 but can be disposed between the flat sheet glass 81 and the liquid crystal cell 5.

As described above, according to this embodiment, the optical anisotropy measurement position at the liquid crystal layer 7 can be easily shifted by rotating the second flat sheet glass. Further, by changing the thickness and/or the refractive index of the second flat sheet glass, the rate of the measurement position shift at the liquid crystal layer 7 relative to the rotation angle of the glass 91 can be changed.

Further, as the uniaxial aligning treatment direction for the liquid crystal layer 7 is generally in a direction perpendicular to the rotation axis of the liquid crystal cell 5, this embodiment allows a measurement position shift in a direction perpendicular to the uniaxial aligning treatment direction.

Now, a tenth embodiment of the present invention will be described with reference to FIG. 10, wherein members identical to those in FIG. 9 are denoted by identical reference numerals, and the description thereof may be omitted.

Referring to FIG. 10, an optical anisotropy measurement apparatus 100 according to this embodiment includes a third flat sheet glass 101 on an optical axis of the incident beam A between the polarizer 2 and the liquid crystal cell 5, so that the sheet glass 101 is supported rotatably about a rotation axis 102 extending in a direction parallel to the rotation axis 8 of the liquid crystal cell 5. The other arrangements are similar to those in the above-mentioned optical anisotropy measurement apparatus 90.

Incidentally, in FIG. 10, the third flat sheet glass 101 is disposed between the polarizer 2 and the second flat sheet glass 91 but can be disposed between the second flat sheet glass 91 and the flat sheet glass 81.

As a preparatory step for measuring an optical anisotropy of a liquid crystal by using an optical anisotropy measurement apparatus according to the present invention, it is ordinarily necessary to adjust the apparatus so that the incident beam A passes through the rotation axis 8 of the liquid crystal cell 5 at a rotation angle 0 deg. of the liquid crystal cell 5.

For the above purpose, according to this embodiment, the third flat sheet glass 101 may be rotated, e.g., in an arrow E direction, whereby it becomes possible to easily effect an adjustment to satisfy the condition that the incident beam A is incident to the rotation axis 8 of the liquid crystal cell 5.

The above-mentioned various embodiments can be appropriately combined, whereby the optical anisotropy of an object to be examined can be measured under various conditions. Further, as already mentioned, the above-described various embodiments of the optical anisotropy measurement apparatus according to the present invention can be used for the optical anisotropy measurement according to either the crystal rotation method or the Senarmont method by simply modifying some members or by disposing some members modifiably.

What is claimed is:

1. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatable about a rotation axis extending perpendicular to the straight line, a polarizer positioned between the light source and the object to be examined, an analyzer positioned between the object to be examined and the photodetector, said analyzer having a polarization direction extending in parallel with that of said polarizer, and an optical member disposed between the light source and the object to be examined so as to cause the beam to pass through an intersection of said straight line and said rotation axis.

2. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said photodetector detecting a phase difference between ordinary rays and extraordinary rays respectively having passed through the object to be examined, said optical anisotropy measurement apparatus further comprising:

a supporting member for supporting the object to be examined rotatable about a rotation axis extending perpendicular to the straight line, a polarizer positioned between the light source and the object to be examined, an analyzer positioned between the object to be examined and the photodetector, said analyzer being supported rotatable about an axis in parallel with said straight line, and an optical member disposed between the light source and the object to be examined so as to cause the beam to pass through an intersection of said straight line and said rotation axis.

3. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

an incident optical system between the light source and the object to be examined, said incident optical system being disposed movably in a direction of said straight line, a supporting member for supporting the object to be examined rotatable about a rotation axis extending perpendicular to the straight line, a polarizer positioned between the light source and the object to be examined, an analyzer positioned between the object to be examined and the photodetector, a pair of transparent members each having a curved surface and a flat surface disposed so as to sandwich the object to be examined with their opposing flat surfaces.

4. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

an incident optical system between the light source and the object to be examined, said incident optical system having a positive power, a supporting member for supporting the object to be examined rotatable about a rotation axis extending perpendicular to the straight line, a polarizer positioned between the light source and the object to be examined, an analyzer positioned between the object to be examined and the photodetector, a pair of transparent members each having a curved surface and a flat surface disposed so as to sandwich the object to be examined with their opposing flat surfaces.

5. An apparatus according to claim 4, wherein said incident optical system comprises at least one convex lens.

6. An apparatus according to claim 5, wherein said incident optical system provides a convergent beam showing an F-number in the range of $\pi/5\lambda$ to $3\pi/2\lambda$ ($\mu m^{-1}$), wherein $\lambda$ denote the wavelength of a beam incident to the incident optical system.

7. An apparatus according to claim 4, wherein said incident optical system provides a convergent beam having a curvature center coinciding with that of said curved surface of the transparent member.

8. An apparatus according to claim 7, wherein said transparent member has a curvature center coinciding with the intersection of said straight line and said rotation axis.

9. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

an incident optical system between the light source and the object to be examined, said incident optical system comprising at least one stop means, a supporting member for supporting the object to be examined rotatably about a rotation axis extending perpendicular to the straight line, a polarizer positioned between the light source and the object to be examined, an analyzer positioned between the object to be examined and the photodetector, said analyzer having a polarization direction extending in parallel with that of said polarizer, a pair of transparent members each having a curved surface and a flat surface disposed so as to sandwich the object to be examined with their opposing flat surfaces.

10. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatable about a rotation axis extending perpendicular to the straight line, a polarizer positioned between the light source and the object to be examined, an analyzer positioned between the object to be examined and the photodetector, a pair of transparent members each having a curved surface and a flat surface disposed so as to sandwich the object to be examined with their opposing flat surfaces, said object to be examined being disposed movably along at least one of the flat surfaces of the transparent members.

11. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatable about a rotation axis extending perpendicular to the straight line, a polarizer positioned between the light source and the object to be examined, an analyzer positioned between the object to be examined and the photodetector, a first exit optical system between said object to be examined and said analyzer, said first exit optical system converting a beam passing through the analyzer into a parallel beam, and an optical member disposed between the light source and the object to be examined so as to cause the beam to pass through an intersection of said straight line and said rotation axis.

12. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatable about a rotation axis extending perpendicular to the straight line, a polarizer positioned between the light source and the object to be examined, an analyzer positioned between the object to be examined and the photodetector, an exit optical system between said analyzer and said photodetector, said exit optical system converting an incident beam to the photodetector into a convergent beam, and an optical member disposed between the light source and the object to be examined so as to cause the beam to pass through an intersection of said straight line and said rotation axis.

13. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector; said optical anisotropy measurement apparatus further including:

a supporting member for supporting the object to be examined rotatably about a first rotation axis extending perpendicular to the straight line, a polarizer positioned between the light source and the object to be examined, an analyzer positioned between the object to be examined and the photodetector, and a first flat transparent sheet member positioned between the light source and the object to be examined and supported rotatably about a second rotation axis extending parallel to said first rotation axis.

14. An apparatus according to claim 13, wherein said object to be examined has a cell structure comprising a substance having an optical anisotropy between a pair of substrates, and at least one of the substrates has a refractive index and a thickness equal to those of said first flat transparent sheet member.

15. An apparatus according to claim 14, wherein said substance having an optical anisotropy is a liquid crystal.

16. An apparatus according to any one of claims 13–15, further including means for rotating said first flat transparent sheet member at an equal angular speed as and in a reverse direction with respect to said object to be examined.

17. An apparatus according to claim 16, further including a second flat sheet member supported between said light source and said object to be examined rotatably about a third rotation axis extending in a direction perpendicular to the first rotation axis.

18. An apparatus according to claim 16, further including a third flat sheet member supported between said light source and said object to be examined rotatably about a fourth rotation axis extending in a direction parallel to the first rotation axis.

19. An optical anisotropy measurement method comprising the steps of:

providing an optical anisotropy measurement apparatus including a light source emitting a light beam, a photodetector disposed opposite to the light source, the photodetector detecting a phase difference between ordinary rays and extraordinary rays respectively having passed through the object to be examined, a supporting member for supporting an object to be examined rotatably about a rotation axis extending perpendicular to a straight line connecting the light source and the photodetector, a polarizer positioned between the light source and the object to be examined, an analyzer positioned between the object to be examined and the photodetector, and an optical member disposed between the light source and the object to be examined so as to cause the beam to pass through an intersection of the straight line and the rotation axis; and measuring an optical anisotropy of the object to be examined, the object being disposed between the light source and the photodetector, by using the optical anisotropy measurement apparatus provided in said providing step.

20. A method according to claim 19, wherein said object to be examined comprises a liquid crystal.

21. A process for producing a liquid crystal device comprising the steps of:

manufacturing a liquid crystal device;

providing an optical anisotropy measurement apparatus including a light source emitting a light beam, a photodetector disposed opposite to the light source, a supporting member for supporting the liquid crystal device, manufactured in said manufacturing step, rotatably about a rotation axis extending perpendicular to a straight line connecting the light source and the photodetector, a polarizer positioned between the light source and the liquid crystal device, an analyzer positioned between the liquid crystal device and the phohotodetector, and an optical member disposed between the light source and the liquid crystal device so as to cause the beam to pass through an intersection of said straight line and said rotation axis, and measuring an optical anisotropy of the liquid crystal device, the liquid crystal device being disposed between the light source and the photodetector, by using the optical anisotropy measurement apparatus provided in said providing step.

22. An optical anisotropy measurement method comprising the steps of:

providing an optical anisotropy measurement apparatus including a light source emitting a light beam, a photodetector disposed opposite to the light source, the photodetector detecting a phase difference between ordinary rays and extraordinary rays respectively having passed through the object to be examined, a supporting member for supporting the object to be examined rotatably about a rotation axis extending perpendicular to a straight line connecting the light source and the photodetector, a polarizer positioned between the light source and the object to be examined, an analyzer positioned between the object to be examined and the photodetector, and a pair of transparent members each having a curved surface and a flat surface disposed so as to sandwich the object to be examined with their opposing flat surfaces; and measuring an optical anisotropy of the object to be examined, the object being disposed between the light source and the photodetector, by using the optical anisotropy measurement apparatus provided in said providing step.

23. A method according to claim 22, wherein the object to be examined comprises a liquid crystal.

24. A process for producing a liquid crystal device including the steps of:

manufacturing a liquid crystal device;

providing an optical anisotropy measurement apparatus including a light source emitting a light beam, a photodetector disposed opposite to the light source, a supporting member for supporting the liquid crystal device, manufactured in said manufacturing step, rotatably about a rotation axis extending perpendicular to a straight line connecting the light source and the photodetector, a polarizer positioned between the light source and the liquid crystal device, an analyzer positioned between the liquid crystal device and the photodetector, and a pair of transparent members each having a curved surface and a flat surface disposed so as to sandwich the liquid crystal device with their opposing flat surfaces; and measuring an optical anisotropy of the liquid crystal device, the liquid crystal device being disposed between the light source and the photodetector, by using the optical anisotropy measurement apparatus provided in said providing step.

25. An optical anisotropy measurement method comprising the steps of:

providing an optical anisotropy measurement apparatus including a light source emitting a light beam, a photodetector disposed opposite to the light source, a supporting member for supporting the object to be examined rotatably about a first rotation axis extending perpendicular to a straight line connecting the light source and the photodetector, a polarizer positioned between the light source and the object to be examined, an analyzer positioned between the object to be examined and the photodetector, and a first flat transparent sheet member positioned between the light source and the object to be examined and supported rotatably about a second rotation axis extending parallel to the first rotation axis; and measuring an optical anisotropy of the object to be examined, the object being disposed between the light source and the photodetector, by using the optical anisotropy measurement apparatus provided in said providing step.

26. A method according to claim 25, wherein the object to be examined comprises a liquid crystal.

27. A process for producing a liquid crystal device comprising the steps of:

manufacturing a liquid crystal device;

providing an optical anisotropy measurement apparatus including a light source emitting a light beam, a photodetector disposed opposite to the light source, a supporting member for supporting the liquid crystal device, manufactured in said manufacturing step, rotatably about a first rotation axis extending perpendicular to a straight line connecting the light source and the photodetector, a polarizer positioned between the light source and the liquid crystal device, an analyzer positioned between the liquid crystal device and the photodetector, and a first flat transparent sheet member positioned between the light source and the liquid crystal device and supported rotatably about a second rotation axis extending parallel to the first rotation axis; and measuring an optical anisotropy of the liquid crystal device, the liquid crystal device being disposed between the light source and the photodetector, by using the optical anisotropy measurement apparatus provided.

28. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatably about a rotation axis extending perpendicular to the straight line, a polarizer positioned between the light source and the object to be examined, an analyzer positioned between the object to be examined and the photodetector, said analyzer having a polarization direction extending in parallel with that of said polarizer, and a pair of transparent members each having a curved surface and a flat surface disposed so as to sandwich the object to be examined with their opposing flat surfaces.

29. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said photodetector detecting a phase difference between ordinary rays and extraordinary rays respectively having passed through the object to be examined, said optical anisotropy measurement apparatus further comprising:

a supporting member for supporting the object to be examined rotatably about a rotation axis extending perpendicular to the straight line, a polarizer positioned between the light source and the object to be examined, an analyzer positioned between the object to be examined and the photodetector, said analyzer being supported rotatably about an axis in parallel with said straight line, and a pair of transparent members each having a curved surface and a flat surface disposed so as to sandwich the object to be examined with their opposing flat surfaces.

30. An apparatus according to claim 2 or 29, further including a quarter wave plate disposed between said object to be examined and said analyzer.

31. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatably about a rotation axis extending perpendicular to the straight line, a polarizer positioned between the light source and the object to be examined, an analyzer positioned between the object to be examined and the photodetector, a first exit optical system between said object to be examined and said analyzer, said first exit optical system converting a beam passing through the analyzer into a parallel beam, and a pair of transparent members each having a curved surface and a flat surface disposed so as to sandwich the object to be examined with their opposing flat surfaces.

32. An optical anisotropy measurement apparatus including a light source emitting a light beam and a photodetector disposed opposite to the light source, for measuring an optical anisotropy of an object to be examined disposed between the light source and the photodetector so as to intersect a straight line connecting the light source and the photodetector, said optical anisotropy measurement apparatus further comprising:

a supporting member for supporting the object to be examined rotatably about a rotation axis extending perpendicular to the straight line, a polarizer positioned between the light source and the object to be examined, an analyzer positioned between the object to be examined and the photodetector, an exit optical system between said analyzer and said photodetector, said second exit optical system converting an incident beam to the photodetector into a convergent beam, and a pair of transparent members each having a curved surface and a flat surface disposed so as to sandwich the object to be examined with their opposing flat surfaces.

33. An apparatus according to any one of claims 3, 4, 9, 10, 28, 29, 31, or 32, wherein said pair of transparent members contact the object to be examined via a liquid having a refractive index almost equal to those of the transparent members.

34. An apparatus according to claim 33, wherein said liquid has a refractive index differing from those of the transparent members by a difference within range of ±0.05.

35. An apparatus according to claim 33 or 34, wherein said object to be examined has a cell structure comprising a substance having an optical anisotropy between a pair of substrates.

36. An apparatus according to claim 35, wherein said liquid has a refractive index almost equal to those of the substrate.

37. An apparatus according to claim 36, wherein said liquid has a refractive index differing from those of the substrates by a difference within range of ±0.05.

38. An apparatus according to claim 35, wherein said substance having an optical anisotropy is a liquid crystal.

39. An apparatus according to any one of claims 1, 2, 3, 4, 9, 10, 11, 12, 28, 29, 31, or 32, wherein said object to be examined has a cell structure comprising a substance having an optical anisotropy between a pair of substrates.

40. An apparatus according to claim 39, wherein said substrate having an optical anisotrophy is a liquid crytal.

* * * * *

UNITED STATES PATENT AND TRADEMARK OFFICE
CERTIFICATE OF CORRECTION

PATENT NO. : 5,903,352

DATED : May 11, 1999

INVENTOR(S) : YOSHINORI OHSAKI, ET AL.

It is certified that error appears in the above-identified patent and that said Letters Patent is hereby corrected as shown below:

COLUMN 1,
Line 66, "light" should read --light,--.

COLUMN 9,
Line 64, "5'" should read --5,--.

COLUMN 19,
Line 50, "rotatable" should read --rotatably--.

COLUMN 26,

Line 51, "crytal" should read --crystal--.

Signed and Sealed this

Twenty-first Day of December, 1999

Attest:

Q. TODD DICKINSON

Attesting Officer       Acting Commissioner of Patents and Trademarks